(12) United States Patent
Bilbie et al.

(10) Patent No.: US 8,232,418 B1
(45) Date of Patent: Jul. 31, 2012

(54) METHOD FOR THE PREPARATION OF LECITHIN

(75) Inventors: James Bilbie, London (CA); Roman Blaszczyk, London (CA)

(73) Assignee: Corn Products International, Inc., Westchester, IL (US)

( * ) Notice: Subject to any disclaimer, the term of this patent is extended or adjusted under 35 U.S.C. 154(b) by 467 days.

(21) Appl. No.: 12/512,299

(22) Filed: Jul. 30, 2009

Related U.S. Application Data

(60) Provisional application No. 61/085,505, filed on Aug. 1, 2008.

(51) Int. Cl.
*C07F 9/02* (2006.01)

(52) U.S. Cl. .................................................... 554/83

(58) Field of Classification Search ..................... 554/83
See application file for complete search history.

(56) References Cited

U.S. PATENT DOCUMENTS

| | | | |
|---|---|---|---|
| 5,166,376 A | 11/1992 | Suzuki et al. | |
| 5,248,799 A | 9/1993 | Schmutzler | |
| 5,597,602 A * | 1/1997 | Peter et al. | 426/478 |
| 5,696,278 A | 12/1997 | Segers | |
| 6,140,519 A | 10/2000 | Hutton et al. | |
| 6,172,248 B1 | 1/2001 | Copeland et al. | |
| 6,426,423 B1 | 7/2002 | Copeland et al. | |
| 6,441,209 B1 | 8/2002 | Copeland et al. | |

OTHER PUBLICATIONS

List, G.R., et al., "Effect of Degumming Conditions on Removal and Quality of Soybean Lecithin," *JAOCS*, Oct. 1981, pp. 892-898.

* cited by examiner

*Primary Examiner* — Deborah D Carr
(74) *Attorney, Agent, or Firm* — Foley & Lardner LLP

(57) ABSTRACT

This technology relates to a method of producing light color lecithin from a lecithin-containing oil, such as crude vegetable oil. The method comprises heating the oil to a suitable temperature, contacting the oil with a peroxide solution, separating the lecithin precipitate from the oil and drying the lecithin. In a specific embodiment, the lecithin produced by the process is corn lecithin.

19 Claims, No Drawings

METHOD FOR THE PREPARATION OF LECITHIN

CROSS-REFERENCE TO RELATED APPLICATIONS

This application claims priority to U.S. Provisional Patent Application No. 61/085,505, filed Aug. 1, 2008, the entire contents of which are hereby incorporated by reference in its entirety.

TECHNICAL FIELD

The present technology relates to methods of processing food and industrial products. In particular, the present technology relates to a method of producing light color lecithin from a lecithin-containing oil.

BACKGROUND

The following description is provided to assist the understanding of the reader. None of the information provided or references cited is admitted to be prior art to the present invention.

Lecithin is a mixture primarily composed of choline, fatty acids, glycerol, glycolipids, triglycerides, carbohydrates and phospholipids (e.g., phosphatidylcholine, phosphatidylethanolamine, phosphatidylserine and phosphatidylinositol). It can be found in egg yolks and the plasma membrane of plant and animal cells, and may be isolated either from egg yolk or from vegetable oils such as soy, safflower, or corn oil, from which it is extracted chemically or mechanically.

Lecithin is used as an emulsifying and stabilizing agent in the food (e.g., margarine, chocolate production), pharmaceutical, and cosmetic (e.g., creams, lipsticks, conditioners, soaps) industries. It is an integral part of cell membranes, is readily metabolized, and as it is regarded as a natural emulsifier, is widely accepted and used in the food industry. It is also applied as an emulsifying, wetting, and dispersing agent for paints and printing inks and widely used in many other industries as an emulsifying, antioxidant and defoaming agent. The U.S. Food and Drug Administration identifies lecithin as Generally Recognized as Safe (21 CFR 184.1400). Lecithin phospholipids can form either liposomes, bilayer sheets, micelles, or lamellar structures, depending on parameters such as degree of hydration, temperature and composition. This results in an amphoteric type of surfactant and finds use in a variety of industries. Pharmacological use of lecithin includes treatment for neurological disorders, dementias, liver ailments and hypercholesterolemia.

Lecithin can be obtained from a source such as extracted oil of plant seeds, e.g., vegetable oil, by using a process known as degumming. Degumming is the treatment of oils with water to remove phosphorus-containing compounds, waxes and other impurities from oil. Degumming converts the phospholipids/phosphatides to hydrated gums which are insoluble in oil and can be separated.

SUMMARY

In accordance with one aspect, the present disclosure provides a method of producing lecithin from a lecithin-containing oil, such as crude vegetable oil. In one embodiment, the disclosure provides a method comprising heating the oil to a suitable temperature, contacting the oil with peroxide solution, then separating and drying the lecithin. In a specific embodiment, the lecithin produced by the method is corn lecithin. In particular embodiments, the methods produce a lecithin with a desirable color and odor, which can be used in a variety of food and pharmaceutical applications.

In one embodiment, the disclosure provides a method of producing lecithin from a lecithin-containing oil comprising: (a) heating the oil to a temperature of less than about 80° C.; (b) contacting the oil with peroxide solution, wherein the lecithin precipitates from the oil; (c) separating the lecithin; and (d) drying the lecithin at a temperature of less than about 70° C.

In one embodiment, the peroxide solution is contacted with the oil such that the final concentration of peroxide in oil is about 0.01% to about 8% by weight of oil. In another embodiment, the peroxide solution is contacted with the oil such that the final concentration of peroxide in oil is about 0.01% to about 3% by weight of oil.

In one embodiment, the lecithin-containing oil is heated to a temperature from about 30° C. to about 80° C. In one embodiment, the oil is heated to a temperature from about 5° C. to about 65° C. In one embodiment, the oil is heated to a temperature of no more than about 80° C.

In one embodiment, the lecithin-containing oil is selected from the group consisting of: rapeseed oil, rice bran oil, rice bran oil, corn fiber oil, corn oil, olive oil, barley oil, soybean oils, oat bran oil, cottonseed oil, canola oil, sunflower seed oil, palm oil, peanut oil, safflower oil, cashew nut oil, kapok seed oil and dill oil. In a suitable embodiment, the crude vegetable oil is corn oil.

In one embodiment, the methods further comprise the step of separating the lecithin precipitate from the oil mixture. For example, the separation may be by centrifugation or decantation.

In one embodiment, the lecithin is dried at a temperature from about 40° C. to about 70° C. In one embodiment, the lecithin is dried at a temperature from about 40° C. to about 80° C. In another embodiment, the lecithin is dried at a temperature from about 55° C. to about 65° C. In one embodiment, the lecithin is dried at a pressure in the range from about 2 to about 250 mm Hg. In one embodiment, the lecithin is dried at a pressure in the range from about 2 to about 200 mm Hg.

In one embodiment, the lecithin is produced in the absence of acid. In one embodiment, the lecithin has greater than about 30% acetone insoluble (AI) matter. In another embodiment, the lecithin has greater than about 99% AI matter. In one embodiment, the lecithin has an acid value of less than about 45 mg KOH/gram. In one embodiment, the lecithin has a moisture content from about 0% to about 6%. In one embodiment, the lecithin has a Gardner scale color measurement of about 16 or lower on an undiluted sample. In another embodiment, the lecithin has a Gardner scale color measurement of about 11 or lower on an undiluted sample and a moisture value of less than approximately 6%.

In another aspect, the disclosure provides a lecithin produced by a method comprising heating the oil and/or lecithin solution to a suitable temperature, contacting the oil with peroxide solution, then separating and drying the lecithin. In a particular embodiment, the disclosure provides a corn lecithin produced by a method comprising heating corn oil to a suitable temperature, contacting the oil with peroxide solution, then separating and drying the corn lecithin.

DETAILED DESCRIPTION

In one aspect, the present disclosure provides a method of producing lecithin. The method includes preparing lecithin from a lecithin-containing oil comprising: (a) heating the oil to a suitable temperature; (b) contacting the oil with a peroxide solution, wherein the lecithin precipitates from the oil; (c) removing the lecithin precipitate from the oil, and; (d) drying the lecithin at a suitable temperature.

As used herein, the term "lecithin-containing oil" refers to any crude solution of phospholipids/phosphatides, such as crude vegetable oil or other lecithin solution. In particular embodiments, the oil can be derived from all types of plant materials such as, e.g., oil from both genetically-modified plants as well as non-genetically modified plants.

The starting material (i.e., crude vegetable oil) can be obtained by methods known in the art, such as, e.g., extraction from the plant parts such as the seeds or germ. For example, in corn wet milling, the main components of the corn kernel (i.e., germ, fiber, gluten, starch, and water soluble compounds) are separated after steeping in water containing sulfurous acid. After about 20 to about 40 hours of steeping, the water soluble matter are separated from residual corn material and further evaporated to about 50% dissolved solids while the kernels are ground and screened to remove germ and fiber. Gluten and starch are further separated by centrifuging. The screened germ is washed and dried. Oil from dry germ is removed by mechanical or solvent extraction. The solids are separated and typically used as animal feed while the oil is removed from residual solids.

Mechanical extraction of oil involves pressing plant materials with the use of a press such as a continuous screw press. Alternatively, solvent extraction involves the use of volatile solvents such as hexane in a continuous or batch mode to extract the oil from the source. The extracted oil is then subjected to a process called degumming to separate the gums (lecithin) from the oil. The quality and composition of lecithin may be affected by the various processes preceding degumming of the oil such as the method of extraction, refining, etc.

In one embodiment, the degumming process involves separation of the phospholipids/phosphatides from the lecithin-containing oil by the addition of water. Many lecithins obtained from sources other than soy have traditionally tended to be dark in color with accompanying strong odors or flavors and, therefore, considered lower value products. Therefore, unlike soy lecithin, some of the other lecithins have very limited use in the food, pharmaceutical, dietetic or cosmetic industry. Some of these, such as corn lecithin have gone exclusively into animal feed or other industrial applications, or are discarded. Although lecithin obtained from these sources is basically a mixture of various phospholipids, the actual composition and quality depend on the origin and processing method of the lecithin.

Soy oil is by far the most important source of lecithin to date. Other oil-bearing seeds such as corn, sunflower and rapeseed yield lecithins, but have historically been considered to be of lesser commercial importance. However, since soy has been recognized as one of the top 8 allergens in the US (Food Allergen Labeling and Consumer Protection Act of 2004), all food products containing soy ingredients, including soy lecithin, require specific allergen labeling. Since alternate lecithin sources such as sunflower, rapeseed and corn are not listed among the top 8 allergens, no such labeling is required. The FALCPA has generated interest in non-soy sources of lecithin. The present inventors discovered a method which can produce a corn lecithin equivalent in quality to a typical soy lecithin. This corn lecithin product has the advantage of being light in color without an unpleasant odor, unlike typical corn lecithins. The methods can also be applied to other vegetable oils, including soy oils, to yield a high quality product.

Conventionally, degumming has been conducted by two methods: water degumming and acid degumming. In a water degumming process, the oil is heated to about 70-90° C., water is added in the amount of 1-2% per weight of oil and mixed for 15-30 minutes. The water soluble phospholipids and hydrophilic components are then separated from the oil by centrifuging and drying. Acid degumming involves treatment of oil with phosphoric or citric acid. Usually, phosphoric acid is added at a quantity between 0.05 and 0.2% of the weight of the oil, to convert the nonhydratable phospholipids to hydratable phospholipids. For example, see U.S. Pat. Nos. 6,426,423; 6,441,209; 6,172,248; 6,140,519; 5,696,278; 5,248,799; and 5,166,376, which are incorporated herein by reference.

In one embodiment, the disclosure provides a method of producing lecithin from a lecithin-containing oil: (a) heating the oil to a temperature of less than about 80° C.; (b) contacting the oil with peroxide solution, wherein the lecithin precipitates from the oil; (c) separating the lecithin precipitate from the oil, and; (d) drying the lecithin at a temperature of less than about 80° C.

In some embodiments, the crude vegetable oil is selected from the group consisting of: rapeseed oil, rice bran oil, corn oil, olive oil, barley oil, soybean oils, oat bran oil, cottonseed oil, canola oil, sunflower seed oil, palm oil, peanut oil, safflower oil, cashew nut oil, kapok seed oil and dill oil. In an illustrative embodiment, the crude vegetable oil is corn oil.

In one embodiment, the lecithin-containing oil is heated to a suitable temperature. Peroxide solution is then added to the heated oil and/or lecithin solution for a time sufficient to precipitate lecithin. The precipitate is separated by known techniques such as decantation, filtration or centrifugation and dried at a suitable temperature and pressure to provide lecithin having desired characteristics such as color, odor, AI value, moisture and acid value.

In one embodiment, the lecithin-containing oil is heated from room or ambient temperature to a temperature of less than about 120° C., less than about 110° C., less than about 100° C., less than about 90° C., less than about 80° C., less than about 70° C., less than about 60° C., less than about 50° C., or less than about 40° C. In some embodiments, the oil is heated to a temperature from room or ambient temperature about 30° C. to about 120° C., about 30° C. to about 80° C., about 40° C. to about 70° C., or about 55° C. to about 65° C. In a suitable embodiment, the oil is heated to a temperature of no more than about 80° C.

In some embodiments, the peroxide solution comprises a mixture of peroxide and water. Any type of water can be used. In an illustrative embodiment, the peroxide solution is made from deionized water. In one embodiment, the peroxide solution that is added to the crude oil is in the range of about 1% to about 50% by volume of peroxide, or about 5% to about 25% by volume of peroxide, or about 5% to about 20% by volume of peroxide.

In one embodiment, the final concentration of peroxide in the oil mixture is from about 0.01% to about 8% by weight of oil. In one embodiment, the final concentration of peroxide in the oil mixture is from about 0.01% to about 3% by weight of oil. In one embodiment, the final concentration of peroxide in the oil mixture is from about 0.05% to about 0.5% by weight of oil. In another embodiment, the final concentration of peroxide in the oil mixture is from about 0.1% to about 0.3% by weight of oil.

In one embodiment, the lecithin-containing oil is contacted with a peroxide solution for a period of about 1 min to about 5 hr. In another embodiment, the oil is contacted with a peroxide solution for a period of about 10 min to about 2 hr.

In an illustrative embodiment, the oil is contacted with a peroxide solution for a period of about 30 min to about 1 hr. In some embodiments, the contacting step may include mixing the oil with the peroxide solution. In one embodiment, the lecithin has a final peroxide value of less than about 100 mEq/kg, less than about 80 mEq/kg, less than about 50 mEq/kg, less than about 40 mEq/kg, less than about 20 mEq/kg, or less than about 10 mEq/kg.

In one embodiment, the precipitated lecithin is dried at a material temperature of no more than about 80° C. In another aspect, the lecithin is dried at a material temperature of no more than about 70° C. In yet another aspect, the lecithin is dried at a material temperature of no more than about 60° C. In an illustrative embodiment, the lecithin is dried at a material temperature of no more than about 58° C. In one embodiment, the lecithin separated from the oil mixture is dried at a material temperature from about 40° C. to about 80° C. In another embodiment, the lecithin is dried at a material temperature from about 40° C. to about 70° C. In yet another embodiment, the lecithin is dried at a material temperature from about 55° C. to about 65° C.

In one embodiment, the lecithin is dried under a pressure of from about 2 mm Hg to about 300 mm Hg absolute. In another embodiment, the lecithin is dried under a pressure of from about 15 mm Hg to about 30 mm Hg absolute. In yet another embodiment, the lecithin is dried under a pressure of less than about 30 mm Hg absolute.

In one embodiment, lecithin obtained by the above mentioned process has greater than about 30% AI matter. In specific embodiments, the lecithin obtained has greater than about 50% AI matter. In one embodiment, the lecithin obtained by the processes described herein may have greater than about 90%, about 95%, or about 99% AI matter.

In specific embodiments, the lecithin may be produced in the absence of acid. In one aspect, lecithin obtained by the process has an acid value of less than about 55 mg KOH/gram. In another aspect, the lecithin has an acid value of less than about 45 mg KOH/gram. In yet another aspect, the lecithin has an acid value of less than about 30 mg KOH/gram.

In one embodiment, the lecithin obtained by the process has a moisture content of about 0.01% to 6%. In another embodiment, the lecithin has a moisture content of about 0.1% to about 5%. In an illustrative embodiment, the lecithin has a moisture content of about 0.1% to about 1%.

An advantage of the present method is that the dried lecithin is low in color and odor. Many lecithins obtained from sources other than soy have traditionally tended to be dark in color with accompanying strong odors or flavors and, therefore, considered lower value products. Therefore, unlike soy lecithin, some of the other lecithins have very limited use in the food, pharmaceutical, dietetic or cosmetic industry. Some of these, such as corn lecithin have gone exclusively into animal feed or other industrial applications, or are discarded. However, the present methods produce a corn lecithin with a good quality color and odor. In one embodiment, lecithin obtained by the process has a Gardner color scale, on an undiluted basis, of about 16 or lower. In another embodiment, lecithin has a Gardner color scale, on an undiluted basis, of about 14 or lower. In yet another embodiment, lecithin has a Gardner color scale, on an undiluted basis, of about 11 or lower.

The Gardner color scale is used to measure the color of transparent liquids by means of comparison with numbered glass standards. Typically, the liquid to be tested is poured "as-is" into a clear test tube. The tube is inserted into the colorimeter where it is illuminated so that it can be visually compared side-by-side with numbered color standards. The Gardner color reading for the sample is based on the two standards found to be the closest color match to the sample. An alternate method is to first blend the liquid (e.g., lecithin) with a specified percentage of clear mineral oil (e.g., 10% lecithin: 90% mineral oil) prior to pouring into the test tube and inserting into the colorimeter. The Gardner color is then reported along with the dilution used (AOCS Ja 9-87).

In some embodiments, the lecithin may be subject to further purification steps, including, but not limited to filtration, chromatographic separation, etc. The lecithin may be further separated based on its solubility such as e.g., acetone soluble, ethanol soluble for use in the pharmaceutical industry.

In one embodiment, lecithin produced by the above-mentioned methods has a quality comparable to the standard soy lecithin and can be used in various industries such as in food, dietetic, cosmetic, or pharmaceutical products.

The lecithins produced by the methods of the invention may be used in a wide range of food products as emulsifiers, stabilizers, control crystallization agents, viscosity modifiers, antioxidants, and reducers or replacers of fat. Typical examples of applications of oil-in-water emulsions with lecithin include infant formula, mayonnaise and salad dressing. Water-in-oil emulsions in foods stabilized with lecithin include margarines, low fat spreads, icings and frostings. The lecithins may also be used as wetters and instantizers when handling food powders. The lecithins may be used as viscosity modifiers in confectionery products such as chocolates, caramels and coatings. In some embodiments, the lecithins produced by the methods of the invention are used to control crystallization and improve plasticity, or as releasing and separating agents in food processing. Lecithins may be used to facilitate the separation of a food from contact surfaces. Lecithin may also be applied to the surfaces of food products such as processed cheese slices to prevent them from sticking to each other. Lecithins are used as stabilizers and emulsifiers in many other food products such as baked goods, cheeses, meat and poultry products, dairy and imitation dairy products. Phospholipids, along with a wide range of oils and fats, may be used as ingredients in many cosmetic applications.

In some embodiments, the lecithins of the present invention may be used as nutritional supplements. Phospholipids have been used as nutritional supplements because they have shown beneficial physiological effects. Soy phospholipids mixtures have been shown to reduce elevated blood cholesterol and triacylglycerols. Soy phosphatidylcholine helps in liver detoxification and repair of damaged liver tissue and phosphatidylserine from soybean, brain and other sources improves cognitive functions. When ingested, phospholipids act as emulsifiers in the bile digestive fluid, ensuring fine dispersion of fatty food molecules in the water phase, thus improving digestion and absorption. Phospholipids combined with bioactive substances can enhance their bioavailability such as in the case of long-chain polyunsaturated fatty acids and tocopherol.

Typical applications of lipids in cosmetics include emollients and specific ingredients for skin care and treatment, hair care, make-up and decorative products. Other commonly used lipids in cosmetics include emulsifiers and structured lipids in which phospholipids can be used as coadjuvants. As in pharmaceutical applications, the cosmetic properties of lipids may be increased synergistically when used in combination with phospholipids. See *Phospholipid Technology and Applications*, F. D. Gunstone, 2008.

The present invention, thus generally described, will be understood more readily by reference to the following examples, which are provided by way of illustration and are not intended to be limiting of the present invention.

EXAMPLES

Example 1

Production of Corn Lecithin (High Peroxide)

Crude corn oil (2600 g) was decanted and filtered to remove all solids. The oil was heated to 60° C. and 30% peroxide (65 g) in 40 g of DI water was added (final concentration of about 0.75% peroxide by weight of oil). Moderate mixing was applied for 1 hour, and then the precipitate was separated by centrifugation and dried at 58° C. under 220 mm Hg absolute pressure for 24 hours. After drying, the product was yellow/orange in color with residual moisture (Karl Fisher method) of about 1.5%. The lecithin had the following characteristics:

TABLE 1

Lecithin Characteristics

| | |
|---|---|
| Peroxide Value | 71.9 meq/kg |
| Acetone Insolubles (AI) | 57.9% |
| Acid Value | 43.8 mg KOH/g |
| Gardner Color (undiluted) | $11^-$ |

These results indicate that the methods described herein are useful for the production of high quality corn lecithin.

Example 2

Production of Corn Lecithin (Low Peroxide)

Crude corn oil (2600 g) was decanted and filtered to remove all solids. The oil was heated to 70° C. and 30% peroxide (8.7 g) in 84 g of DI water was added (final concentration of about 0.10% peroxide by weight of oil). Moderate mixing was applied for 1 hour, and then the precipitate was separated by centrifugation and dried at 62° C. under 220 mm Hg absolute pressure for 24 hours. After drying, the Gardner color (undiluted) was $12^+$, while the peroxide value was 30.8 meq/kg. These results indicate that the methods described herein are useful for the production of high quality corn lecithin, even with a relatively low concentration of peroxide.

Example 3

Production of Corn Lecithin: Comparison of Drying Conditions

Crude corn oil (2600 g) was decanted and filtered to remove all solids. The oil was heated to 65° C. and 21.7 g of 30% peroxide dissolved in 82 g of DI water was added to reach 0.25% peroxide by weight of oil. Moderate mixing was applied for 1 hour, and then the precipitate was separated by centrifugation. The sample was divided into 3 portions and dried at 57° C., 72° C. and 80° C. under 220 mm Hg absolute pressure for 24 hours. After drying, the sample dried at 57° C. had a Gardner scale color of 10 (undiluted). The sample dried at 72° C. had Gardner scale color of 15 (undiluted), and sample dried at 80° C. had Gardner scale color of 17 (undiluted). Accordingly, corn lecithin produced by the methods of the present invention has a desirable color suitable for food and pharmaceutical uses.

Example 4

Production of Soy Lecithin

Crude soy oil (2440 g) was decanted and filtered to remove all solids. The oil was heated to 60° C. and 30% peroxide (16.2 g) in 81 g of DI water was added. Moderate mixing was applied for 1 hour, and then the precipitate was separated by centrifugation and dried at 60° C. under 220 mm Hg absolute pressure for 24 hours. The undiluted lecithin Gardner color was 8+. Accordingly, soy lecithin produced by the methods of the present invention has a lower color for a variety of food and pharmaceutical uses.

EQUIVALENTS

The present disclosure is not to be limited in terms of the particular embodiments described in this application, which are intended as illustrations of individual aspects thereof. Many modifications and variations can be made without departing from its spirit and scope, as will be apparent to those skilled in the art. Functionally equivalent embodiments within the scope of the disclosure, in addition to those enumerated herein, will be apparent to those skilled in the art from the foregoing descriptions. Such modifications and variations are intended to fall within the scope of the claims, along with the full scope of equivalents to which such claims are entitled. It is to be understood that this disclosure is not limited to particular methods, reagents, compounds or compositions, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

The various aspects and embodiments disclosed herein are for purposes of illustration and are not intended to be limiting, with the true scope and spirit being indicated by the following claims.

What is claimed is:

1. A method of extracting lecithin from a lecithin-containing oil comprising:
   (a) heating the oil to a temperature of less than about 80° C.;
   (b) contacting the oil with a peroxide solution, wherein the lecithin precipitates from the oil;
   (c) separating the lecithin precipitate from the oil, and;

(d) drying the lecithin at a material temperature of less than about 80° C.

2. The method of claim 1, wherein the peroxide solution is contacted with the oil such that the final concentration of peroxide in oil is about 0.01% to about 5% by weight of oil.

3. The method of claim 1, wherein the peroxide solution is contacted with the oil such that the final concentration of peroxide in oil is about 0.01% to about 3% by weight of oil.

4. The method of claim 1, wherein the oil is heated to a temperature from about 30° C. to about 80° C.

5. The method of claim 1, wherein the oil is heated to a temperature no more than about 80° C.

6. The method of claim 1, wherein the oil is corn oil.

7. The method of claim 1, wherein the oil is selected from the group consisting of: rapeseed oil, rice bran oil, rice bran oil, corn fiber oil, corn oil, olive oil, barley oil, soybean oils, oat bran oil, cottonseed oil, canola oil, sunflower seed oil, palm oil, peanut oil, safflower oil, cashew nut oil, kapok seed oil and dill oil.

8. The method of claim 1, further comprising the step of separating the lecithin precipitate from the oil.

9. The method of claim 8, wherein the separating is by centrifugation or decantation.

10. The method of claim 8, wherein the lecithin is dried at a material temperature from about 40° C. to about 80° C.

11. The method of claim 8, wherein the lecithin is dried at a material temperature from about 55° C. to about 65° C.

12. The method of claim 8, wherein the lecithin is dried at a pressure from about 2 to about 250 mm Hg absolute.

13. The method of claim 1, wherein the lecithin is produced in the absence of acid.

14. The method of claim 1, wherein the lecithin has greater than about 30% acetone insoluble (A.I.) matter.

15. The method of claim 14, wherein the lecithin has greater than about 99% acetone insoluble (A.I.) matter.

16. The method of claim 1, wherein the lecithin has an acid value of less than about 45 mg KOH/gram.

17. The method of claim 1, wherein the lecithin has a moisture content from about 0% to about 6%.

18. The method of claim 1, wherein the lecithin has a Gardner color scale of about 18 or lower on an undiluted basis.

19. The method of claim 18, wherein the lecithin has a Gardner color scale of about 11 or lower on an undiluted basis.

* * * * *